US00PP09125P

United States Patent [19]

Kohl, deceased et al.

[11] Patent Number: Plant 9,125

[45] Date of Patent: May 2, 1995

[54] AZALEA HYBRID PLANT 'PAUL A. KOHL'

[76] Inventors: Paul A. Kohl, deceased, late of St. Louis, Mo.; by Rosalie K. Buckley, Successor Trustee, 3641 Flora Pl., St. Louis, Mo. 63110

[21] Appl. No.: 210,711

[22] Filed: Mar. 18, 1994

[51] Int. Cl.[6] ..... A01H 5/00
[52] U.S. Cl. ..... Plt./56
[58] Field of Search ..... Plt. 55, 56, 57

[56] References Cited

PUBLICATIONS

Wayside Garden Spring Catalogue, 1993, Hodges, S.C.

White Flower Farm 1991 Spring Catalogue, Litchfield, Conn.

Winterthur Museum and Garden 1992 Spring Catalogue, Winterthur, Delaware.

*Primary Examiner*—James R. Feyrer

[57] ABSTRACT

The new plant is a hybrid semi-evergreen azalea characterized by compact mounded, branching form and blooms which appear in clusters of two with an occasional cluster of three. The azalea blooms in early April to mid-May in St. Louis, Mo. Blooms measure 1 32/32 to 2 15/32 inches in diameter, usually 1 32/32 to 2 15/32 inches, and are single with five lobes fused at the base with 10 non-petaloid stamens. The blooms are uniform pink with no flecking.

2 Drawing Sheets

BACKGROUND OF THE INVENTION

The present invention relates to a new and distinct variety of semi-evergreen azalea of the genus Rhododendron and a member of the Ericaceae family. It was produced by Paul A. Kohl as a side interest to his work as a horticulturist. The plant was selected by him from a group of seedlings which resulted from his cross-pollination of various species. He continued to produce identical plants in St. Louis, Mo. by means of cuttings from the original seedling.

The value of this new cultivar lies in its uniform color, fine shape, adaptability to the heavy soil of the St. Louis area, and its hardiness in a place notorious for the extremes of a capricious climate.

The specific parentage of the new variety is unknown because the hybridizer kept no known records of the background, parentage and crosses which resulted in the new plant.

The applicant has compared it to similar plants offered in plant catalogues and several known examples. The Azalea hybrid "Paul A. Kohl" appears to be an "azalea mucronatum". The flower shape is similar to *Rhododendron schlippenbachii,* the "Royal Azalea", but *schlippenbachii* is lighter pink with white stamens and pistil while Azalea hybrid plant "Paul A. Kohl" has pink stamens and Rhodium pistil. *Schlippenbachii* is more open-branched while the subject cultivar is very compact.

Working from a catalogue from "Wayside Gardens", the color of the flower is similar to "Ellie Harris" which shows the deep red pistil. "Ellie Harris" is a hose-in-hose azalea; the subject plant is single and of deeper color.

Azalea hybrid plant "Paul A. Kohl" resembles "Gables Tall Lavender" #892299 except that "Gables" has red speckling on uppermost petal while Azalea hybrid plant "Paul A. Kohl" has no visible variation in color.

The subject azalea is similar to the "Torch Azalea", *Rhododendron kaempferi* "Atlanta", but this flower is a deeper pink with slight speckling and a more pointy and narrower leaf.

This new hybrid has the following combination of characteristics which distinguish it from other varieties:

1. Flower color is a completely uniform pink with no variant shading, giving it a formal appearance. Flower size is 1 31/32 to 2 15/32 inchs, usually 1 31/32 to 2 5/32 inches from petal tip to petal tip. It blooms from early April to mid-May, depending on the season.

2. The plant is vigorous in growth and exceptionally hardy, withstanding years of cold, heat, drought and excessive moisture experienced in the St. Louis area. The plant has survived temperatures as low as −10° F. and periods of consecutive days below the zero mark. The plant has survived a sudden drop in temperature from warm days at the end of October to 8° F. on the eighth of November. This acute change killed many other plants in and around St. Louis.

3. Ease of vegetative propogation by softwood cuttings: The plant was successfully propagated by Paul A. Kohl in St. Louis, Mo., and the specimens that he propagated are those shown in the accompanying photographs. Paul A. Kohl tested the plant in St. Louis and determined it to be stable. Each clonal progeny exhibited identical characteristics of the mother plant, establishing the hybrid as reproducible and true to type.

DESCRIPTION OF THE PHOTOGRAPHS

DETAILED PLANT DESCRIPTION

Color determinations are based on "The Color Chart issued by the British Color Council in collaboration with The Royal Horticultural Society". The French "Repetoire de Coleurs" was also consulted.

Origin: Hybrid Seedling.
Parentage: Unknown.
Classification: Hybrid.

Form: Globose.

Habit: Dense and very compact with ascending branches. As plant matures its width becomes only slightly greater than its height, thus maintaining its globular shape.

Plant vigor: Active, strong, rapid growth on plant's own root stock. On older plants, the growth is between 3 $\frac{1}{8}$ and 3 15/16 inches per year while on new cuttings, the growth measured between 4 $\frac{1}{4}$ and 5 $\frac{7}{8}$ inches in the second year.

Figure 1:
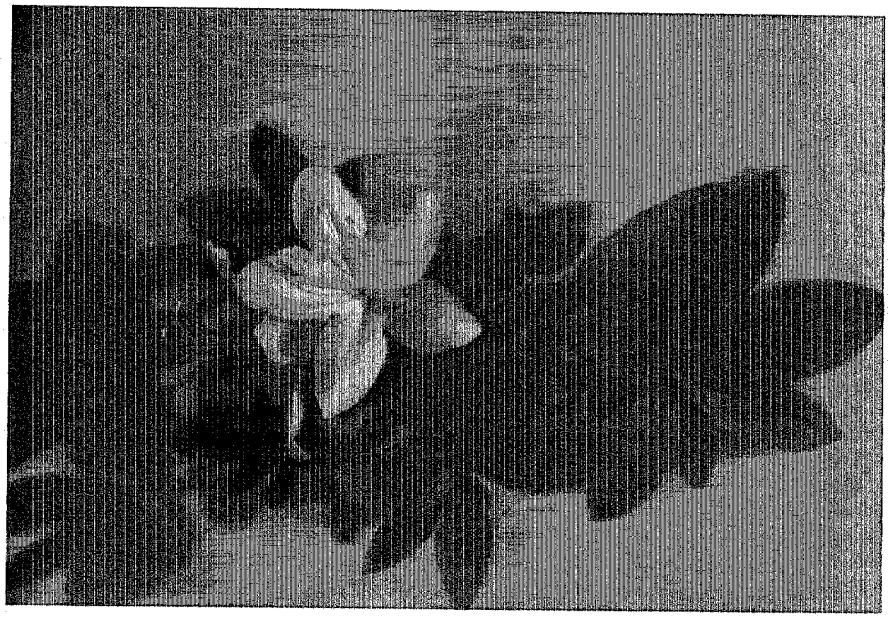
FIG. 1 is a close up showing the flower color and form and foliage.
Figure 2:
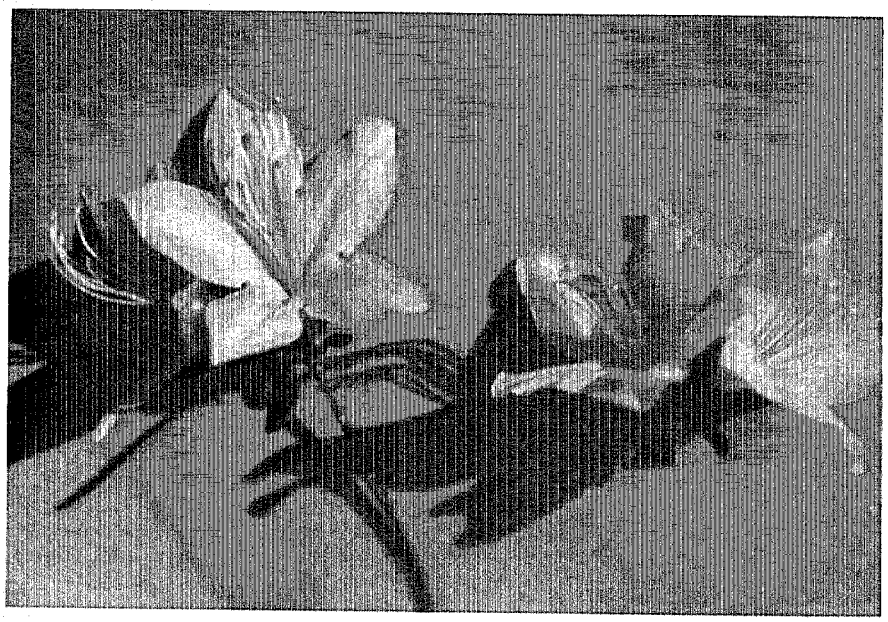
FIG. 2 is a close up of the flower without foliage.
Figure 3:
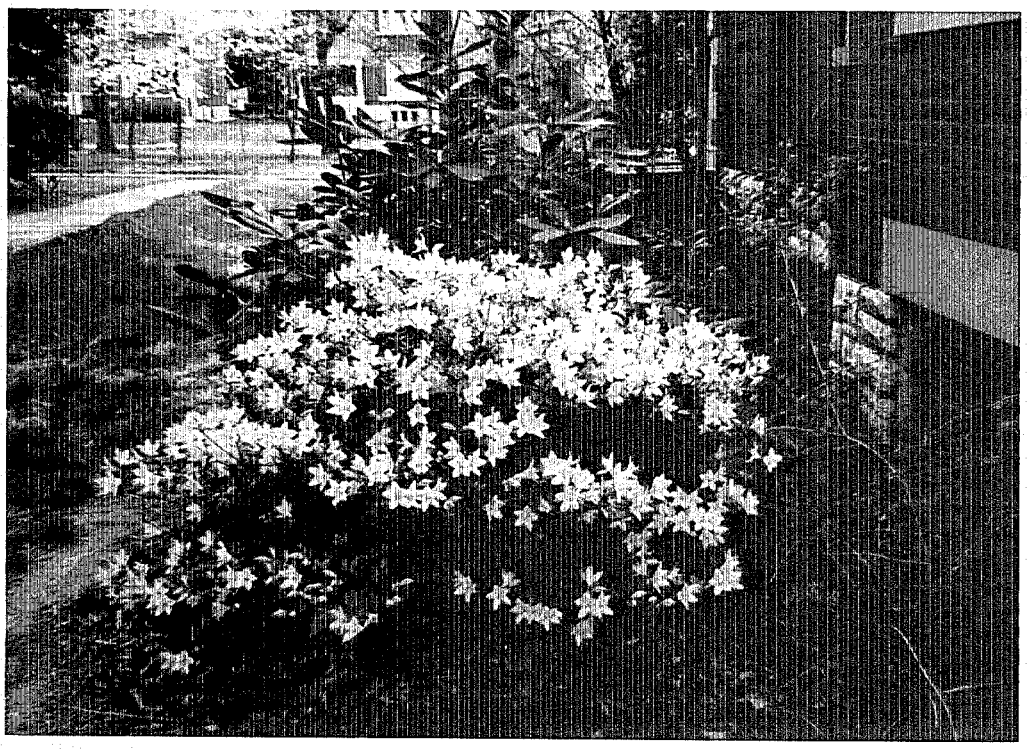
FIG. 3 is a photograph of a plant in bud stage.
Figure 4:
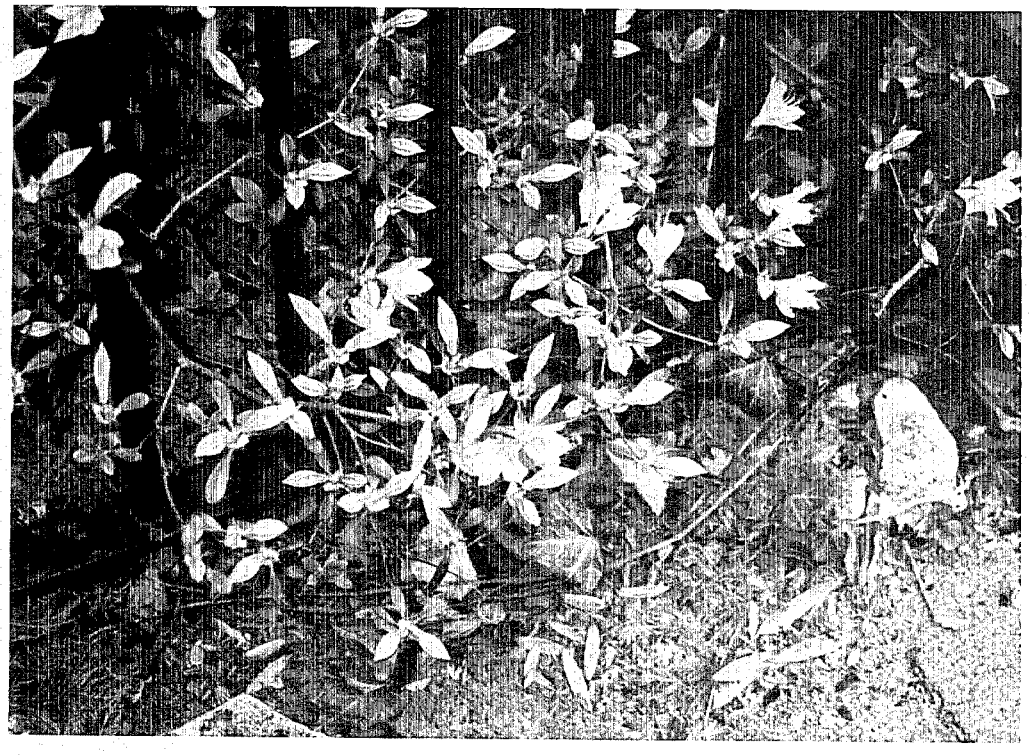
FIG. 4 is a photograph of a mature plant used as a foundation plant showing the overall habit.

Size: Height of a mature ten (10) year old plant is 3 $\frac{1}{2}$ feed with a width of about 4 feet. The plant reached its full height in between eight and ten years (FIG. 4). Two-year old cuttings are between 12 and 15 inches in height and 11 inches in width.

Blooming habit: Prolific. The plant covers itself with blooms as shown in FIG. 4.

Blooming period: Blooms appear from early April to mid-May in the St. Louis area depending on the severity and lateness of the season.

Rooting: Cuttings from plant root easily. In a test, cuttings were taken on August 6, and were rooted by August 15.

HARDINESS

Azalea hybrid plant "Paul A. Kohl" azalea has withstood temperatures to −10° F. It has not suffered any severe frost damage. During the period of extreme cold referred to previously, there was one year when most azaleas in the area were either killed or failed to bloom. The subject azalea bloomed on all its lower branches and although the blooms failed on the upper branches, the plants themselves showed no real damage on the crown, and leaves formed properly.

FOLIAGE

Arrangement: Opposite and whorled.

Type: Semi-evergreen.

Shape: Ovate, obtuse, flat.

Size: Average length of mature leaf (from petiole to leaf apex) is 2 11/32 to 2 17/32 inches.

Color:

*Mature growth upper surface.*—Spinach Green Group 960.

*New Leaf growth.*—Spinach Green Group 960/2.

Margins: Entire.

Texture: Smooth

Stems: New growth is pale green, maturing to brown, slightly hairy or pubescent, not perfectly smooth. It is not tomentose or reticulate or seabrous.

BUDS

Flower buds: Elliptic and not hairy. Color Group #530 Amaranth, Rose, B7. Bud is not significantly different from the mature flower. It is broadly ovate and obtuse.

Calyx: Persistent and hairy throughout. Five imbricated, hairy sepals are joined at base to form a cup.

INFLORESCENCE

Flower: Complete and perfect. Sepals do not fall off as buds open.

Blooming period: Plant blooms from early April to mid-May in the St. Louis area, depending on the mildness or severity of the season.

How borne: In clusters of two with an occasional cluster of three.

Size: Small to medium, being 1 31/32 to 2 5/32 inches normally and occasionally up to 2 15/32 inches in diameter and 1 9/16 to 1$\frac{3}{4}$ inches in length.

Petalage:

*Color.*—The entire flower is an even pink, Amaranth Rose Group #530—B7. Petals are an even color throughout.

*Form.*—Five lobes fused at base with 10 linear stamens.

*Pedicel.*—Length is $\frac{3}{8}$ inches with greenish hairs.

*Shape.*—Round.

Margin.—Smooth and even, not ruffled.

*Texture.*—Smooth and satiny.

*Persistence.*—Petals hang, dry, turn brown, discolor with age and eventually fall off.

*Fragrance.*—None.

Form: Single with linear stamens, openly funnel-shaped.

Reproductive organs:

*Stamens.*—10 stamens with no variation in this number. Pink anthers with yellow pollen.

*Pistils.*—Single, average length is 1$\frac{3}{8}$ inches, longer than petal length. Color falls into the Rhodamine Pink Group #527. Most exact color is Tyrian Rose #24/1. Closest horticultural example of color is Salvia Gregii.

Ovary.—Five locules within a hypogynous ovary. enclosed by a sericeous ovary wall. Seeds observed to be forming but not fully developed.

*Disease resistance.*—No known disease during growth in St. louis, Mo.

DESCRIPTION OF MOST SIMILAR AZALEA CULTIVARS

Azalea hybrid plant "Paul A. Kohl" has moderate-sized blooms, normally from 1 31/32 to 2 5/32 inches in diameter and occasionally up to 2 15/32 inches in diameter, that are single and of a uniform shade of pink. The plant blooms from early April to mid-May in the St. Louis area, depending on the season. The following cultivars represent those most similar Azalea hybrid plant to "Paul A. Kohl" that the applicant is aware of in the nursery trade:

*Rhododendron schlippenbachii:* Single, pink, 5-petalled flowers 2 15/16 inches in diameter with pale center and white stamens. Early spring bloomer.

Azalea "Ellie Harris": Light pink blossoms, 1 31/32 inches across in hose-in-hose fashion. Mid season bloomer.

Torch azalea *Rhododendron kaempferi* "Atlanta": Deeper pink with light flecks. A pointy, thin leaf. Mid to late bloomer.

Gables tall lavender #892299: Medium pink with bright flecks at upper petal center.

Azalea "Winterthur": Single clear lavender 3 inch blossoms. (Picture in catalogue shows pink blooms, similar to azalea hybrid plant "Paul A. Kohl") Blooms mid-May in Delaware.

REFERENCES

Wayside Gardens Spring Catalogue, 1993, Hodges, S.C.

White Flower Farm 1991 Spring Catalogue, Litchfield, Conn.

Winterthur 1992 Spring Catalogue, Winterthur, Del.

Color Chart issued by the British Colour Council in collaboration with The Royal horticultural Society French Repetoire de Coleurs, Vol. 1

It is claimed:

1. A new variety of hybrid semi-evergreen azalea plant as described and illustrated, characterized by a compact globular form, tolerant of rapid changes in temperature, resistant to drought and excessive moisture, hardy at −10° F. in mid-western United States' seasons, good rooting habit and blooms having a diameter of 1 32/32 to 2 15/32 inches, which appear generally in duplicate with an occasional triplicate, the plant blooms from early Apr. to mid-May in St. Louis, Mo., with single, uniform pink flowers that are of open funnel-shaped form with non-petaloid stamens.

* * * * *